(12) United States Patent
Funk

(10) Patent No.: US 9,001,962 B2
(45) Date of Patent: Apr. 7, 2015

(54) METHOD AND APPARATUS FOR MULTIPLE X-RAY IMAGING APPLICATIONS

(71) Applicant: Triple Ring Technologies, Inc., Newark, CA (US)

(72) Inventor: Tobias Funk, Martinez, CA (US)

(73) Assignee: Triple Ring Technologies, Inc., Newark, CA (US)

( * ) Notice: Subject to any disclaimer, the term of this patent is extended or adjusted under 35 U.S.C. 154(b) by 254 days.

(21) Appl. No.: 13/722,947

(22) Filed: Dec. 20, 2012

(65) Prior Publication Data

US 2014/0177785 A1    Jun. 26, 2014

(51) Int. Cl.
*A61B 6/00* (2006.01)
*A61B 6/03* (2006.01)
*G21K 5/10* (2006.01)

(52) U.S. Cl.
CPC ..................................... *A61B 6/035* (2013.01)

(58) Field of Classification Search
CPC ...... A61B 6/032; A61B 6/4007; A61B 6/037; G06T 11/005; G06T 2211/436
USPC ......... 378/4, 9, 21, 55, 62, 196; 382/128, 131
See application file for complete search history.

(56) References Cited

U.S. PATENT DOCUMENTS

| | | | |
|---|---|---|---|
| 5,550,378 A | 8/1996 | Skillicorn et al. |
| 5,610,967 A | 3/1997 | Moorman et al. |
| 5,644,612 A | 7/1997 | Moorman et al. |
| 5,651,047 A | 7/1997 | Moorman et al. |
| 5,682,412 A | 10/1997 | Skillicorn et al. |
| 5,729,584 A | 3/1998 | Moorman et al. |
| 5,751,785 A | 5/1998 | Moorman et al. |
| 5,808,306 A | 9/1998 | Skillicorn et al. |
| 5,835,561 A | 11/1998 | Moorman et al. |
| 5,859,893 A | 1/1999 | Moorman et al. |
| 6,060,713 A | 5/2000 | Skillicorn et al. |
| 6,118,853 A | 9/2000 | Hansen et al. |
| 6,118,854 A | 9/2000 | Solomon et al. |
| 6,157,703 A | 12/2000 | Solomon et al. |
| 6,175,611 B1 | 1/2001 | Melen et al. |
| 6,178,223 B1 | 1/2001 | Solomon et al. |
| 6,181,764 B1 | 1/2001 | Solomon et al. |
| 6,183,139 B1 | 2/2001 | Solomon et al. |
| 6,198,802 B1 | 3/2001 | Elliott et al. |
| 6,208,709 B1 | 3/2001 | Melen |
| 6,234,671 B1 | 5/2001 | Solomon et al. |
| 6,649,914 B1 | 11/2003 | Moorman et al. |
| 7,062,006 B1 | 6/2006 | Solomon et al. |

(Continued)

OTHER PUBLICATIONS

Mazin, S.R., et al., Inverse-geometry volumetric CT system with multiple detector arrays for wide field-of-view imaging. Med Phys, 2007. 34(6): p. 2133-42.

(Continued)

*Primary Examiner* — Nikita Wells
(74) *Attorney, Agent, or Firm* — Sabrina N. David

(57) ABSTRACT

The present invention pertains to an apparatus and method for medical imaging comprising rotating two X-ray source-detector pairs around an axis of rotation simultaneously to quickly acquire image data and form a computed tomography (CT) dataset. The sources can be configured to emit radiation from a plurality of discrete locations. The CT dataset can be utilized as a prior to reconstruct a three-dimensional image from subsequent bi-planar imaging with these source-detector pairs.

14 Claims, 8 Drawing Sheets

(56) References Cited

U.S. PATENT DOCUMENTS

| | | | |
|---|---|---|---|
| 8,761,478 B2* | 6/2014 | Hsieh et al. | 382/131 |
| 2012/0230467 A1* | 9/2012 | Katsumata et al. | 378/19 |
| 2012/0257710 A1* | 10/2012 | Funk | 378/9 |
| 2014/0321606 A1* | 10/2014 | Funk | 378/9 |

OTHER PUBLICATIONS

De Man, B., et al., An Iterative Maximum-Likelihood Polychromatic Algorithm for CT. IEEE Transactions on Medical Imaging, Oct. 2001. 20(10): p. 999-1008.

* cited by examiner

METHOD AND APPARATUS FOR MULTIPLE X-RAY IMAGING APPLICATIONS

FIELD OF THE INVENTION

The present invention pertains to X-ray imaging systems. It particularly pertains to interventional X-ray imaging systems.

BACKGROUND

X-ray imaging procedures have not only become the standard for many diagnostic applications in the medical field but have also seen increasing use across a variety of surgical or interventional applications. Interventional procedures are less invasive alternatives to open surgery wherein implements are inserted through relatively small incisions or natural orifices. Interventional procedures can be performed under X-ray guidance by using X-ray fluoroscopy systems that provide real-time projection images. Increasingly interventional specialists are relying on 3-D images for intraoperative guidance and verification, such as images acquired by computed tomography (CT). In contrast to clinical CT scanners these images are acquired at relatively slow rotation speeds and typically have lower image quality than clinical CT scans.

In some cases interventional specialists may use bi-planar fluoroscopy systems. In these systems two single-plane fluoroscopic systems can image the patient from two different angular positions. Advantages of using such systems include the ability to provide the interventional specialist with additional spatial information and to reduce the amount of contrast agent that needs to be injected into the patient in order to view a contrast-highlighted internal feature from multiple angles.

Radiation exposure can be a concern with all X-ray imaging techniques. Concern has grown for fluoroscopy and CT in particular due to their relatively high levels of radiation exposure. While the benefits of these techniques can outweigh the risks of radiation exposure, provide imaging equipment that performs the imaging task at lower dose. A drawback of some low-dose systems is a relatively small field of view, limiting use to cardiac applications.

What is needed is an X-ray imaging system that can address the need for 3-D images during interventional procedures and is flexible enough for multiple interventional imaging applications. What is further needed is a low dose imaging system for interventional imaging applications.

SUMMARY

The present invention pertains to a method of medical imaging comprising forming a computed tomography dataset by acquiring image data from two source-detector pairs while rotating the pairs simultaneously through non-overlapping sets of angles around an axis of rotation. The sets of angles can be at least 90 degrees each, and the rotations may be completed in less than 3 seconds by a motor or other element. Additional image data can also be acquired from the source-detector pairs while stationary and positioned at a predetermined angle relative to one another, and the computed tomography dataset can be used for registration of this image data. The predetermined angle may space the source-detector pairs between 80 and 100 degrees apart around an imaging volume. Sources of the source-detector pairs may be configured to emit radiation from a plurality of discrete locations on their faces or may be point sources. In the former case, the computed tomography dataset may also be used as a prior, e.g. a Bayesian prior, for reconstruction of a three-dimensional image from the additional image data and for correction of image artifacts. A three-dimensional reconstruction from the image data acquired with the source-detector pairs in static positions may be completed with a maximum-likelihood maximization in voxel space, in and ordered-subset maximization framework, or with a maximum likelihood algorithm for transmission tomography.

The sources of source-detector pairs may be configured such that less than 10 cm exists between the pluralities of discrete emissive locations when the sources are positioned as near as possible. This configuration may allow a relatively large field of view. The source-detector pairs may also be configured to image a region of interest with higher exposure relative to other regions of the imaging volume.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

Figure 1:
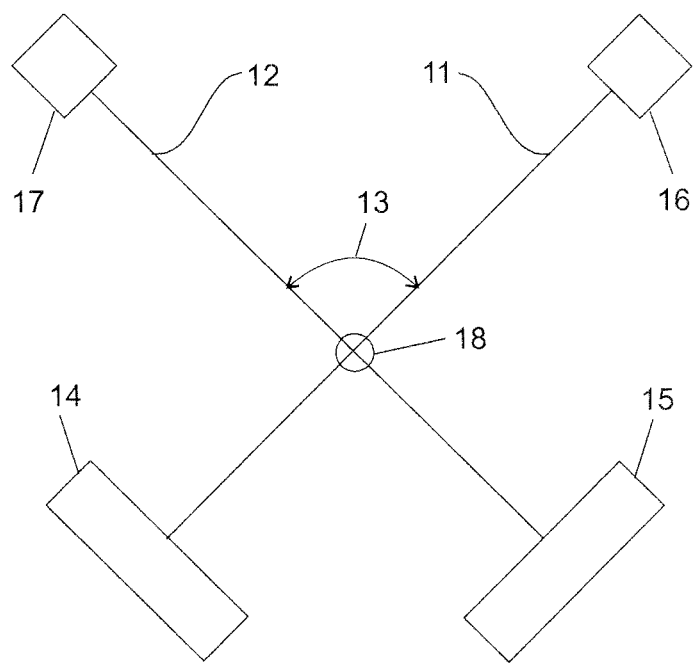
FIG. 1 is a diagram representing two source-detector pairs of an embodiment of the present invention.

FIG. 1 is a diagram representing two source-detector pairs of an embodiment of the present invention. Embodiments of the present invention may feature two or three X-ray sources and two or three X-ray detectors. In FIG. 1 a first source 14 and a first detector 16 are positioned such that the face of first source 14 and the face of first detector 16 may be parallel and separated by a distance long enough to accommodate a patient or subject for imaging. A second source 15 and a second detector 17 may be similarly positioned relative to one another; the face of second source 15 may be parallel to the face of second detector 17 with a distance long enough to accommodate imaging subjects maintained between them. A first axis 11 has been drawn connecting the centers of the faces of first source 14 and first detector 16, and a second axis 12 has been drawn connecting the centers of the faces of second source 15 and second detector 17. These axes may be physical, e.g. beams or other supports, or non-physical, e.g. maintained by maintaining the spatial relationship of a source and detector relative to one another. For example, in embodiments of the present invention medical C-arms, U-shaped arms, O-arms, physical axes of other shapes, tracks along which source and detector motion can be confined, closed gantries, or any other mechanical structure may be used to maintain the fixed distances between, orientations of, and rotations about an isocenter by two source-detector pairs.

In some embodiments of the present invention, the distance maintained between source and detector in source-detector pairs can be 3, 4, 5, 6, 7, 8, 9, 10, 11, 12, 13, 14, 15, 16, 17, 18, 19, or 20 inches, or any non-integer number of inches between these enumerated values. These embodiments of the present invention may be particularly useful for the imaging of extremities, including but not limited to podiatric, dental, and similar imaging applications. In some embodiments of the present invention, the distance maintained between source and detector in source-detector pairs can be between 20 inches and 120 inches, 30 inches and 100 inches, or 40 inches and 70 inches, inclusive, and any other integer or non-integer number of inches within the enumerated ranges. For example, the distance may be 30, 31, 32, 33, 34, 35, 36, 37, 38, 39, 40, 41, 42, 43, 44, 46, 46, 47, 48, 49, 50, 51, 52, 53, 54, 55, or 56 inches, or any non-integer number of inches between the enumerated values.

A point of overlap 18 between first axis 11 and second axis 12 may correspond to an isocenter of the system, e.g. a point at which an X-ray beam traveling from the center of the face of first source 14 to the center of the face of first detector 16 would intersect an X-ray beam traveling from the center of the face of second source 15 to the center of the face of second detector 17. While angle 13 between first axis 11 and second axis 12, relating to the separation between the two sources or between the two detectors, may change, the isocenter of the system can remain fixed in space at point of overlap 18.

In one embodiment of the present invention, first source 14 and second source 15 may be point sources, wherein X-rays are emitted from a single discrete point on the face of the source. A point source may be an X-ray tube or any other means of emitting X-ray radiation from a small discrete point. In this embodiment, first detector 16 and second detector 17 may be any type of X-ray detecting sensors, including but not limited to flat-panel detectors or image intensifier systems.

In another embodiment of the present invention, first source 14 and second source 15 may be multi-focal spot sources, wherein X-rays can be emitted from a plurality of discrete locations of the face of the source. A multi-focal spot source may be array of carbon nanotubes, a scanning beam source, a scanning laser source, an array of single cathode emitters, or any other source capable of emitting radiation from a plurality of discrete locations on its face. First detector 16 and second detector 17 may be any type of X-ray detecting sensor including but not limited to fast photon-counting detectors. One example of a multi-focal spot source and photon-counting detector combination that may be utilized in this embodiment of the present invention is disclosed in U.S. Pat. No. 5,729,584 entitled "Scanning Beam X-ray Imaging System" and hereby incorporated by reference.

The faces of sources and detectors in embodiments of the present invention may also be circular, square, polygonal, rectangular, trapezoidal, triangular, or any other shape. Embodiments of the present invention utilizing multi-focal spot sources may comprise source faces of diameters or widths ranging from 1" to 5", 5" to 10", 10" to 15", or 15" to 20", inclusive, or any other integer or non-integer number of inches within the enumerated ranges. Embodiments of the present invention utilizing pixelated detectors in conjunction with multi-focal spot sources may comprise detectors of diameters or widths ranging from 1 to 2 cm, 2 to 3 cm, 3 to 4 cm, 4 to 5 cm, 5 to 6 cm, 6 to 7 cm, 7 to 8 cm, 8 to 9 cm, 9 to 10 cm, 10 to 11 cm, 11 to 12 cm, 12 to 13 cm, 13 to 14 cm, 14 to 15 cm, 15 to 16 cm, 16 to 17 cm, 17 to 18 cm, 18 to 19 cm, or 19 to 20 cm, inclusive, or any non-integer number of centimeters between the enumerated values.

Embodiments of the present invention utilizing point X-ray sources may emit X-rays from an emissive point or spot having a diameter or width of 0.1 mm to 5 mm, inclusive. Emissive points or spots may further have a width, diameter, or full-width at half maximum between 0.1 mm and 0.5 mm, 0.5 mm and 1.0 mm, 1.0 mm and 2.0 mm, 2.0 mm and 3.0 mm, 3.0 mm and 5.0 mm, or any other integer or non-integer number of millimeters within the enumerated ranges. Diameters or widths may also be larger than 5.0 mm, though image resolution may degrade with increasing focal spot size. Embodiments of the present invention utilizing point sources may comprise detectors of widths or diameters of 0 to 10 cm, 10 to 20 cm, 20 to 30 cm, 30 to 40 cm, 40 to 50 cm, or 50 to 60 cm, inclusive, or any other integer or non-integer number of centimeters within the enumerated ranges. For example, detectors may have widths or diameters of 15, 16, 17, 18, 19, 20, 21, 22, 23, 24, 25, 26, 27, 28, 29, 30, 31, 32, 33, 34, or 35 cm, inclusive, or any non-integer number of centimeters between the enumerated values. It is possible that detector widths or diameters may be greater than 60 cm for some applications.

In embodiments of the present invention comprising multi-focal spot source, each source-detector pair may provide tomosynthetic image data due to the plurality of focal spots on the source face; a specific plane or multiple planes within the field of view of a given source-detector pair may be reconstructed. System comprising multi-focal spot sources can also demonstrate superior contrast-to-noise and lower patient exposure at a given level of image quality compared to point-source, or shadowgraph, systems, as detectors can be smaller and collect less scattered radiation.

Figure 2:
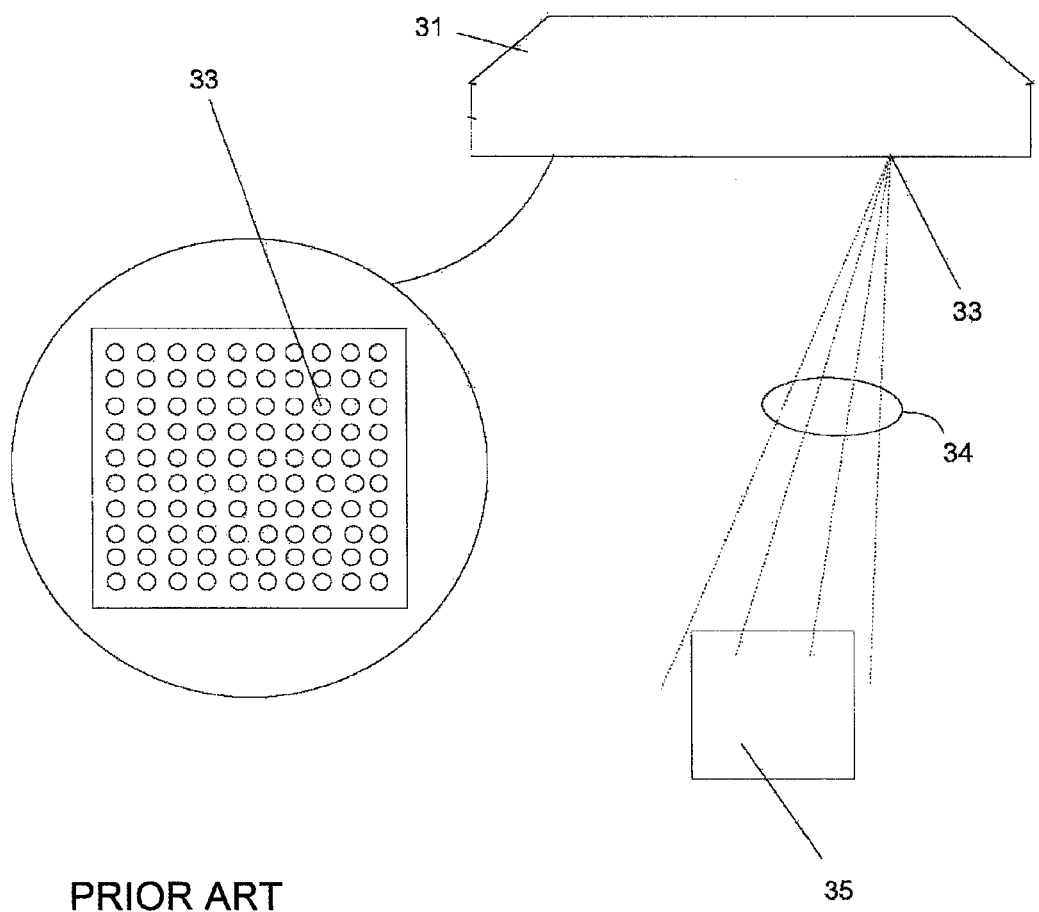
FIG. 2 is a diagram illustrating a source-detector pair comprising a multi-focal spot source and small detector of one embodiment of the present invention.

FIG. 2 is a diagram illustrating a source-detector pair comprising a multi-focal spot source and small detector of one embodiment of the present invention. Source 31 can project beams of radiation from a plurality of discrete locations towards a detector. For example, a beam 34 can be emitted from a discrete focal spot 33 and configured to illuminate detector 35.

Figure 3:
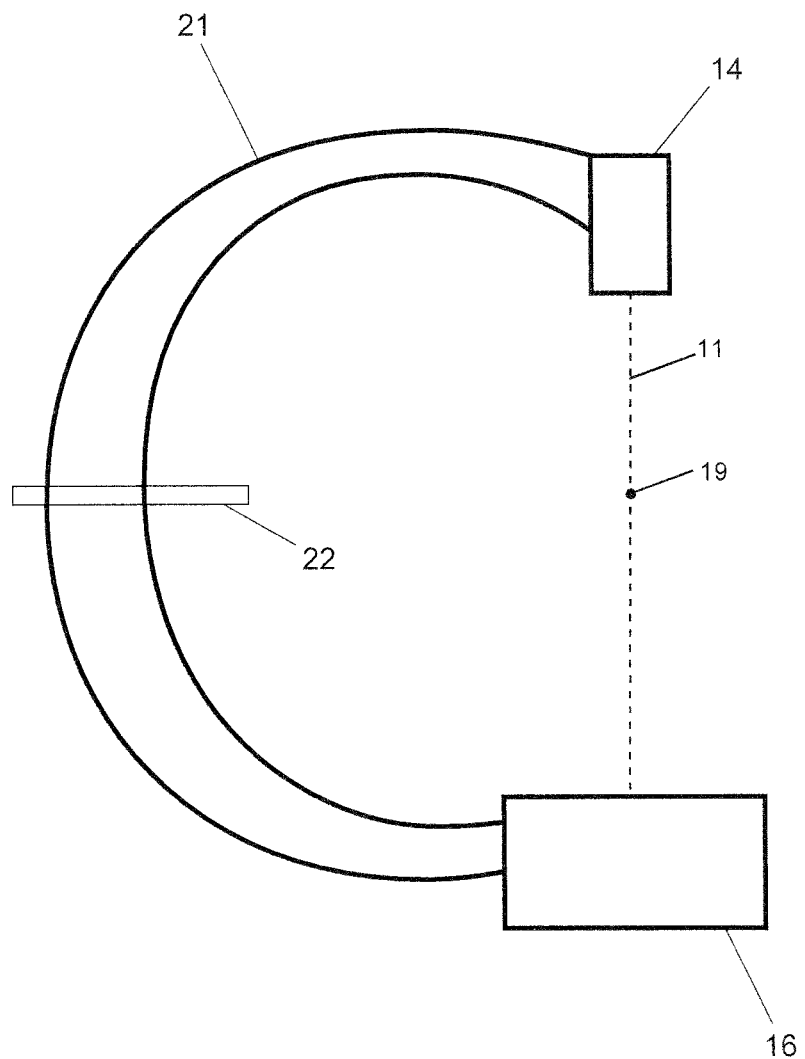
FIG. 3 is a diagram showing an X-ray source and X-ray detector mounted on opposing ends of a medical C-arm in one embodiment of the present invention.

In one embodiment of the present invention, the distances and orientations of two X-ray source-detector pairs may be maintained by the sources and detectors being mounted on two medical C-arms. FIG. 3 is a diagram showing an X-ray source and X-ray detector mounted on opposing ends of a medical C-arm in one embodiment of the present invention. A second C-arm holding a second source-detector pair may also be affixed at joint 22. Rotation of the C-arm 21 may occur around a rotation axis through a joint 22 and an isocenter 19 of the system; in the view of FIG. 3, first source 14 and first detector 16 may be rotated into or out of the page. Both C-arms can rotate around a common axis of rotation through a shared isocenter.

An isocenter may or may not be located at the midpoint between a source and detector in a source-detector pair. It may be desirable that a human patient can be positioned at the isocenter of the system so that rotations occur around the patient and the targeted patient volume remains in focus even if the angle between the source-detector pairs changes. In point-source systems imaging performance may be optimized by positioning a patient nearer to the detector than to the source. Therefore, in an embodiment of the present invention comprising point-source systems, source-detector pairs may be connected to one another in a manner that creates a system isocenter closer to the detectors than to the sources. For example, with reference again to FIG. 1, the system may be configures such that point of overlap 18 is nearer to first detector 16 and second detector 17 than first source 14 and second source 15 along first axis 11 and second axis 12, respectively. In tomosynthetic imaging systems, imaging performance may be optimized by positioning a patient nearer to the source than the detector. An embodiment of the present invention comprising tomosynthetic systems may be configured such that a system isocenter is closer to the sources than the detectors of two source-detector pairs.

A visualization of an offset or non-centered isocenter may be a pair of scissors. A pair of scissors is made up of two pieces, each piece typically being a blade with a handle. The handle is typically shorter than the blade, but a joint is usually placed between the handle and the blade, not at the actual midpoint of a piece. Blades and handles rotate around the joint, or isocenter, of the scissors despite differing lengths on either side of the joint.

The curved geometry of C-arms may permit the placement of an area or volume of a patient to be imaged at the isocenter of two source-detector pairs in embodiments of the present invention. A patient may be positioned on a bed or table or otherwise secured within the crook or "C" of the C-arms while imaging occurs. Furthermore, an apparatus to which the two C-arms are affixed may rotate the C-arms around other axes to widen the range of possible patient positions. For example, with reference to FIG. 3, joint 22 may be moved vertically or along a curved track.

The rotation of source-detector pairs around an isocenter, e.g. the change in an angle between the source-detector pairs, may be electronically controllable. For example, an embodiment of the present invention may include an electronically controlled mechanical motor, set of motors, actuators, or other means of rotating the source-detector pairs. The means of rotation may be coupled to an electronic input unit allowing a user to select rotation parameters to be implemented during imaging. Optional input values may also include frame rate, e.g. the frequency at which images are captured, total number of degrees to be rotated, or other imaging-related parameters. Alternatively, an embodiment may be configured to convert a user-selected end-result, e.g. a number of images of a given level of quality taken at specific angular intervals, into appropriate operating parameters, e.g. angular speed, frame rate, etc., required to achieve said end-result. The calculation of operating parameters may account for system-specific capabilities; information regarding the speed at which the imaging system can collect sufficient data for image reconstruction at a given level of quality, the speeds to which axes can be safely accelerated or decelerated, the angles through which axes can rotate without contact between sources and detectors, and so forth may be included in the determination of operating parameters.

Embodiments of the present invention may be used for at least three different imaging procedures: computed tomography (CT), bi-planar imaging, and fluoroscopy. Physicians within an operating room, catheterization lab ("cath lab"), or other facility may wish to perform one, two, or three of these imaging procedures for pre-operative diagnosis, intraoperative guidance, post-operative verification, and other purposes. Embodiments of the present invention with these three different modalities can prove space- and cost-efficient and may also incur speed and image quality benefits compared to single-modality systems.

In a computed axial tomography (CAT) scan a patient may be positioned on a table and slid through an enclosed, circular gantry. An X-ray source and arc of X-ray detectors may be positioned opposite one another inside the gantry and rotated at a high speed to acquire images from a series of different angles or views. A comprehensive three-dimensional image of the imaging volume can be formed by reconstructing the series of views and can be used for identification of cancers, tumors, infarctions, fractures, and other internal conditions. This type of three-dimensional image may be desirable during a medical procedure, for example to accurately position an implement that has been inserted into the patient, e.g. an ablative device or catheter, or to ensure that a medical condition has been sufficiently corrected, e.g. cancer removed or infarction cleared, before completing the surgery and closing incisions. However, during an interventional or surgical procedure positioning a patient for a conventional CAT scan may be difficult or impossible. A CT dataset or image may instead be acquired by rotating a C-arm on opposing ends of which are mounted an X-ray source and an X-ray detector such that the X-ray source and detector can rotate around the patient, sliding an O-arm around the patient within which source and detector rotate, or by similarly lower-profile methods.

To accurately reconstruct a three-dimensional representation of a targeted volume, images may be taken through at least 180 degrees, plus some number of degrees that account for beam properties, around the imaging volume. An intraoperative CT imaging system may be designed to acquire images through the 180 plus degrees as quickly as possible because patient motion between frames, even from a patient's breathing or heartbeat, can introduce motion blurring into individual frames or the final three-dimensional reconstruction. Imaging speed may also be important as patients may be involved in a time-sensitive medical procedure or otherwise ill or injured. The maximum rotational speed safely achievable in intraoperative CT may be significantly lower than in a CAT scan.

In one embodiment of the present invention, two X-ray source-detector pairs may be rotated in a manner such that one source-detector pair can sweep out a number of degrees while the other source-detector pair sweeps out the rest of the degrees necessary to construct a three-dimensional CT image. In this embodiment, the number of views required for the CT reconstruction can be collected in half the time it would have taken a single axis rotating at the same speed to collect the views.

Source-detector pairs may be rotated through any total number of degrees possibly ranging from one to 360 degrees. Reconstructed CT image quality may be enhanced for numbers of degrees greater than 180. Some embodiments of the present invention may rotate source-detector pairs through a total number of degrees between 180 and 185, 185 and 190, 190 and 200, 200 and 205, 205 and 210, or 210 and 215 degrees, inclusive. Some embodiments of the present invention may rotate source-detector pairs through a total number of degrees between 215 and 230, 230 and 245, 245 and 260, 260 and 275, 275 and 290, 290 and 305, or 305 and 320 inclusive. Some embodiments of the present invention may rotate source-detector pairs through a total number of degrees between 320 and 325, 325 and 330, 330 and 335, 335 and 340, 345 and 350, or 355 and 360, inclusive. Source-detector pairs may be initially positioned with any angle between them allowing the predetermined amount of rotation to occur and may be rotated in the same direction or in opposing directions.

The time taken for a single axis carrying a source and detector to rotate through and obtain images at a given set of degrees can be limited by patient safety concerns. Currently, fast C-arm CT scans may take approximately four to six seconds. This speed may increase in the future. Embodiments of the present invention can cut the minimum time required to complete an intraoperative CT in half. For example, if four to six seconds is assumed as a reference time for intraoperative CT with a single source-detector pair, then an intraoperative CT scan using two source-detector pairs may take only 2 to 3 seconds, or less than 3 seconds.

In one embodiment of the present invention, source-detector pairs comprising point-source imaging systems are used to acquire a CT dataset in less than 3 seconds, or half the time that would be required to acquire the dataset with a single source-detector pair. Image data can be acquired at a predetermined number of angles, e.g. views, as the source-detector pairs are rotated, and reconstruction of a three-dimensional image may be accomplished using standard cone-beam reconstruction, multiplanar reconstruction, standard filtered back projection, maximum-likelihood algorithm for transmission tomography, ordered subset expectation maximization, or any other iterative or non-iterative CT reconstruction method or combination of methods.

In another embodiment of the present invention, source-detector pairs comprising multi-focal spot sources are used for acquisition of a CT dataset. The low-dose advantages of multi-focal spot source, e.g. tomosynthetic, systems may be particularly desirable in CT applications as concerns exist regarding the amount of radiation incurred by patients while undergoing CT, a large number of high-quality images providing the most accurate three-dimensional reconstruction, and its effect on the probability of cancer development. Image data collected as the source-detector pairs rotate may be used to generate image planes using shift-and-add reconstruction or other techniques as described in U.S. Pat. No. 6,178,223 entitled "Image reconstruction method and apparatus," hereby incorporated by reference. Reconstruction of a three-dimensional image may be accomplished using maximum likelihood expectation maximization (MLEM); Fourier rebinning with John's equation (FORE-J), which can re-sort image data acquired with a multi-focal spot source to resemble data acquired with a point source; maximum-likelihood algorithm for transmission tomography (ML-TR); ordered subset expectation maximization (OSEM); or any other iterative or non-iterative three-dimensional reconstruction algorithms or combinations thereof.

In one embodiment of the present invention, datasets acquired during a fast C-arm CT scan are reconstructed using an iterative algorithm utilizing the maximum-likelihood algorithm for transmission tomography (ML-TR) as described by De Man et. al. [cite] ML-TR seeks to find a set of linear attenuation coefficients $\{\mu_i\}_{j=1}^{J}$ that maximizes the log-likelihood for a set of measurements $\{y_i\}_{i=1}^{I}$, $$L = \Sigma_{i=1}^{I}(y_i \cdot \ln(\hat{y}_i) - \hat{y}_i)$$

where i denotes a given projection line, j a given pixel, and $\hat{y}$ the expected number of photons detected along projection line i given the current reconstruction $\{\mu_i\}$. It can be shown that $$\mu_j^{n+1} = \mu_j^n + \frac{\sum_{i=1}^{I} l_{ij} \cdot (\hat{y}_i - y_i)}{\sum_{i=1}^{I} l_{ij} \cdot \left[\sum_{h=1}^{J} l_{ih}\right] \cdot \hat{y}_i}$$

maximizes this log-likelihood. The expected number of photons $\hat{y}$ along a given projection line can be calculated as $$\hat{y}_i = b_i \cdot \exp\left(-\sum_{j=1}^{J} l_{ij}\mu_j\right)$$

where the factor $b_i$ can be determined by acquiring images from the source-detector pairs with no imaging volume present.

In a further embodiment, the ML-TR algorithm can be implemented in an ordered-subset maximization (OSEM) framework. This embodiment may improve the computational speed of reconstruction. A principle of OSEM is to perform iterations only for a small subset of angular samples, which may be widely spaced over the angular range. Subsequent iterations can then be performed on different subsets until all angles have been used and one complete iteration has been performed.

In this embodiment of the present invention, the number of subsets utilized may range from one to the number of views acquired, e.g. the number of angles at which an image dataset is acquired, inclusive. The number of subsets utilized may also be 3, 4, 5, 6, 7, 8, 9, 10, 11, 12, 13, 14, 15, 16, 17, 18, 19, 20, 21, 22, 23, 24, or 25. The number of views within a subset may be any number of views between two views and the number of views acquired, inclusive. The number of views in a subset may also be 3, 4, 5, 6, 7, 8, 9, 10, 11, 12, 13, 14, 15, or any other number of views. For example, in one embodiment of the present invention, each of two source-detector pairs can be rotated through 180 degrees and acquire image data, e.g. a view, every 4 degrees such that a total of 90 views over 360 degrees are acquired. A reconstruction algorithm implementing ML-TR in an OSEM framework could then utilize, for example, fifteen subsets, each subset comprising six views, and possibly be run for ten complete iterations.

Embodiments of the present invention may also be used for imaging without rotation of the source-detector pairs, in which case connective axes of the pairs may be fixed at a given angle relative to one another during the imaging process. For bi-planar imaging, the angle between the two source-detector pairs of an embodiment of the present invention may be fixed at any integer or non-integer number of degrees between zero and 180. A near-zero minimum angle and near-180 maximum angle between source-detector pairs in embodiments of the present invention may be determined by the angles at which adjacent edges of the two sources or two detectors come into contact. For example, if the source-detector pairs are multi-focal spot, tomosynthetic systems, angles may be constrained by the edges of the two source faces coming into contact with one another, the sources being the relatively larger elements of source-detector pairs. If the source-detector pairs are point X-ray source imaging system, angles may be constrained by the edges of the two detector faces coming into contact.

The angle between the two source-detector pairs of embodiments of the present invention may be a number of degrees between 0 and 10, 10 and 20, 20 and 30, 30 and 40, 40 and 50, 50 and 60, 60 and 70, 70 and 80, 80 and 90, 90 and 100, 100 and 110, 110 and 120, 120 and 130, 130 and 140, 140 and 150, 150 and 160, 160 and 170, or 170 and 180, inclusive, or any other integer or non-integer number of degrees between the enumerated values.

Bi-planar X-ray imaging may be particularly useful for procedures in which a contrast agent may be inserted into a patient to highlight veins or other features that are not intrinsically opaque to X-ray radiation. It may be desirable to limit the amount of contrast agent injected into a patient as contrast agents have been known in some cases to cause allergic reactions and even kidney failure. When more than one perspective of a feature highlighted by a contrast agent may be useful to a physician, two X-ray imaging systems positioned at different angles around the patient may be utilized for bi-planar image acquisition after a single dose of contrast agent has been administered. Acquiring two views simultaneously can spare the additional dose of contrast agent which may be administered if time were taken to move an X-ray system from one angle to another.

In one embodiment of the present invention, a novel bi-planar imaging system may comprise two multi-focal spot, tomosynthetic imaging systems. Multiple planes between a source and detector can be reconstructed from the data acquired by a single system, and a three-dimensional image or video may be constructed using the data acquired by both systems. Acquisition of a three-dimensional image in this fashion may provide significantly less radiation exposure to the patient compared to collecting projection images through 180 degrees or more around the patient, e.g. compared to computed tomography; this embodiment may allow a surgeon to acquire three-dimensional images frequently during a procedure without concern of excessive radiation dose. Furthermore, this embodiment may enable real-time, e.g. video, imaging, whereas even CAT scans may not acquire data fast enough to generate real-time three-dimensional images.

Reconstruction of a three-dimensional image from two tomosynthetic images in embodiments of the present invention may be accomplished using MLEM, ML-TR, or any other reconstruction algorithm in voxel space. A voxel may be considered the three-dimensional equivalent of a pixel; if a pixel is considered a square area in two-dimensional space, a voxel would be a cubic volume in three-dimensional space. In one embodiment of the present invention, an ML-TR algorithm in an OSEM framework may be utilized to reconstruct a three-dimensional image from two bi-planar images. For example, one subset comprising two views may be utilized.

Three-dimensional reconstruction from two tomosynthetic images may be optimized when the images are acquired with source-detector pairs positioned when the angle between source-detector pairs is between 60 and 120 degrees, 70 and 110 degrees, or 80 and 100 degrees, inclusive, e.g. nearly perpendicular to one another. However, three-dimensional reconstruction from two tomosynthetic images in this embodiment of the present invention may also be accomplished for other angles of separation. For example, angles less than 60 degrees may be optimal if the spatial frequency of an imaging volume is significantly higher in one dimension than in another, e.g. if details of an imaging volume viewable from one direction are much finer than those in a perpendicular view.

Figure 4:
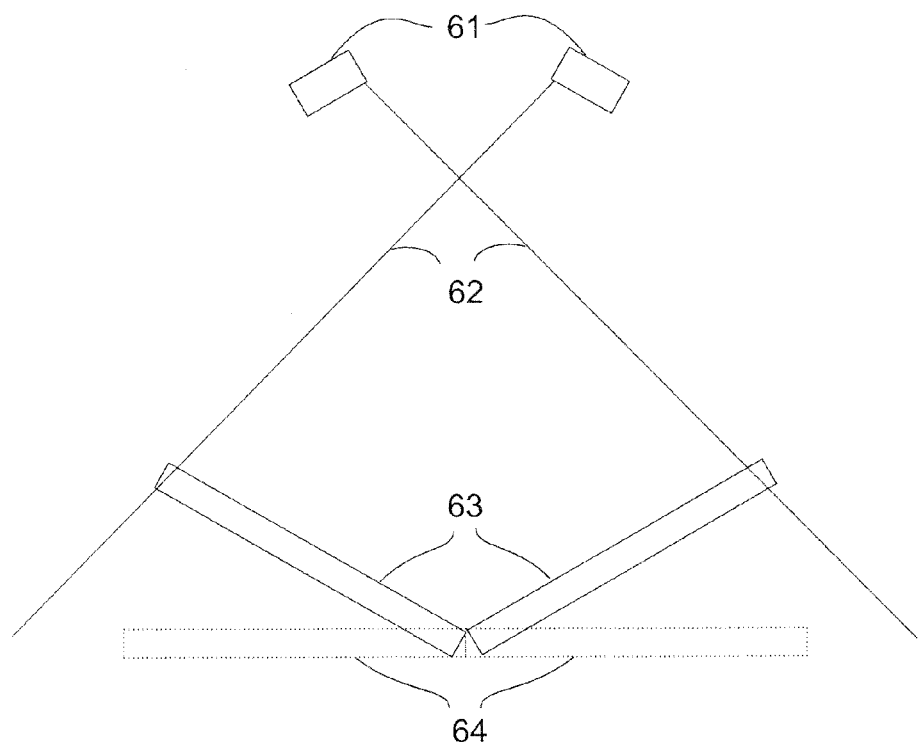
FIG. 4 is a diagram illustrating two source-detector pairs positioned at a minimum number of degrees possible for the given system geometry.

In embodiments of the present invention, the axes of two source-detector pairs may also be fixed at the smallest angle possible given the geometry of the system, e.g. at a near-zero minimum number of degrees as previously discussed. FIG. 4 is a diagram illustrating an embodiment of the present invention with two source-detector pairs positioned at the minimum number of degrees given the source and detector geometry. Faces of two multi-focal spot sources of tomosynthetic source-detector pairs may be in an angled configuration 63. Reconstruction algorithms can account for the imaging geometry created by angled configuration 63 and produce images similar to those that would have been acquired by a single, extended flat detector. This correction can be accomplished using a mask or any other method of correcting for known image distortions. For example, an appropriate assignment of the signals from pixels of detectors 61 into an image plane can be determined analytically or experimentally and can account for the sampling effects of angled configuration 63.

Flat configuration 64 may represent the area that would be subtended by the two multi-focal spot sources shown in angled configuration 63 if they were instead positioned adjacently in the same plane. Outermost X-ray paths 62 between detectors 61 and angled configuration 63 are also shown. X-ray paths 62 are extended past angled configuration 63 into the plane of flat configuration 64 to represent the boundaries of the flat source that is "simulated" by two sources in angled configuration 63. It can be seen that a simulated flat detector can actually be wider than the source area created by flat configuration 64. The size of a multi-focal spot source may be related to the field of view available from an imaging system; the angled configuration that may be created when two source-detector pairs are positioned at a smallest possible angle in embodiments of the present invention may achieve a larger field of view than if a flat source of equivalent surface area were used.

The field of view (FOV) of an imaging system may refer to the dimensions of the region that can be imaged by the system. The FOV of an imaging system may in large part be determined by imaging geometry of the system, including but not limited to the size of one or more of its components, e.g. source or detector, and the distances maintained between the source, detector, and subject during imaging. Despite low-dose and other advantages, tomosynthetic imaging systems utilizing a multi-focal spot source have seen somewhat limited application, primarily being used for cardiac procedure and related imaging, due to their relatively small fields of view. One embodiment of the present invention comprises two tomosynthetic imaging systems, positioned at a near-zero minimum number of degrees. This embodiment may provide a field-of-view large enough for a wider range of applications, including fluoroscopy and interventional procedures on larger tissues and organs of the human body, e.g. cranial, gastrointestinal, or other procedures.

Figure 6:
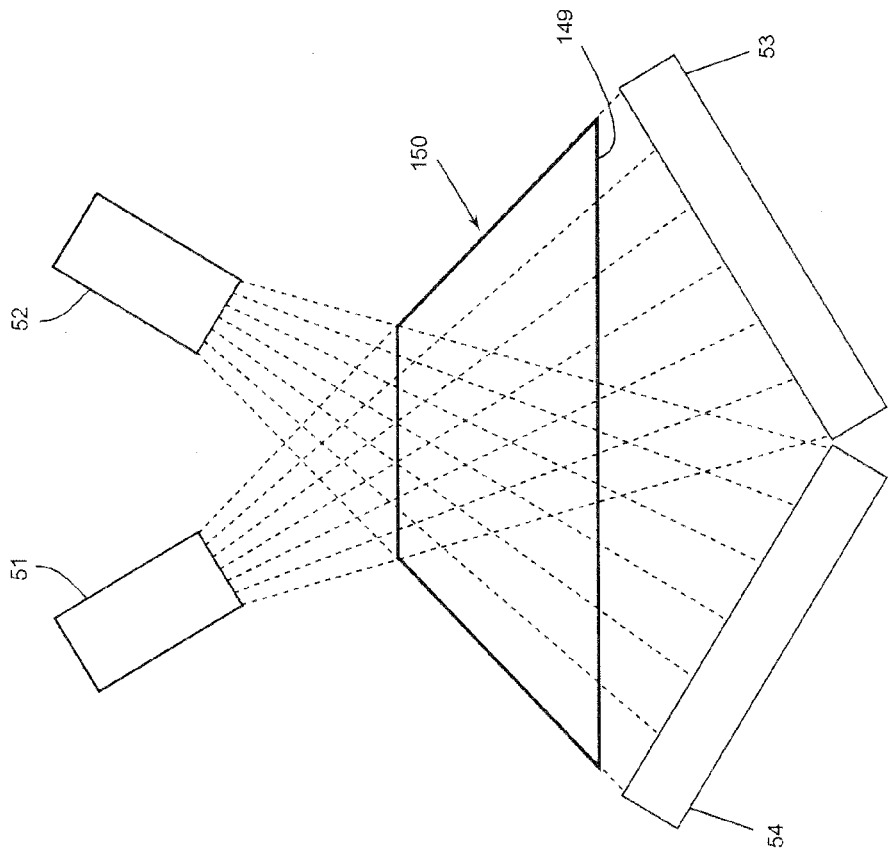
FIG. 6 is a diagram illustrating a field of view of an embodiment of the present invention comprising two source-detector pairs.
Figure 5:
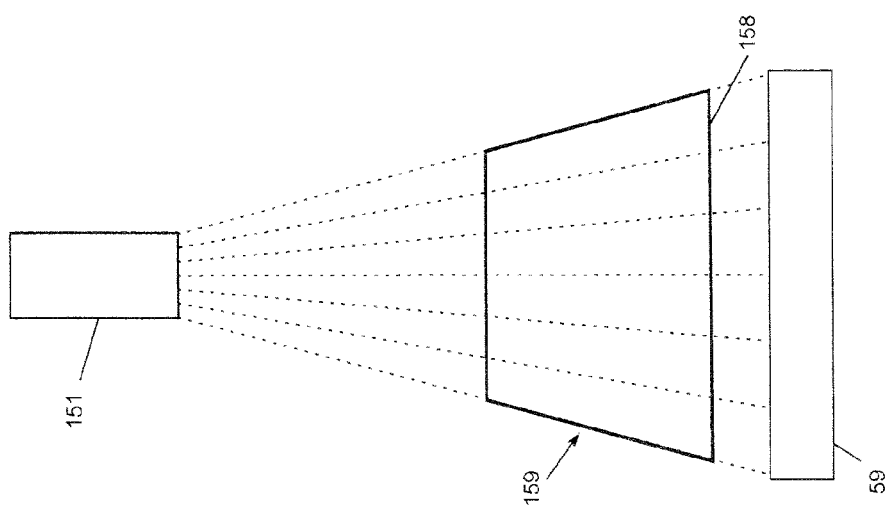
FIG. 5 is a diagram illustrating a field of view of a multi-focal spot, tomosynthetic imaging system.

FIG. 5 is a diagram illustrating a field of view of a multi-focal spot, tomosynthetic imaging system. A possible imaging volume 159 is indicated between large source 59 and small detector 151. It can be seen that the widest field of view 158 may be on the source side of the imaging volume. FIG. 6 is a diagram illustrating a field of view of an embodiment of the present invention comprising two multi-focal spot source-detector pairs. First small detector 51 and second small detector 52 can be illuminated by first large source 53 and second large source 54, respectively. A possible imaging volume 150 of this embodiment may be larger than imaging volume 159 available from a single source-detector pair. Particularly, a maximum field of view 149 may be significantly wider than field of view 158 available from the single source-detector pair. This embodiment may provide a field of view suitable for a broader range of clinical applications than existing tomosynthetic imaging systems.

It can also be seen in FIG. 6 that imaging volume 150 may have regional variations in X-ray flux. A central region of imaging volume 150 may be imaged by both source-detector pairs, whereas outer regions of the imaging volume may be imaged by a single source-detector pair. As the central region may receive twice the amount of X-ray flux relative to outer regions of the imaging volume, reconstructed images may display higher contrast-to-noise ratios and less out-of-plane blurring in the area imaged near the center of the imaging volume relative to the outer edges of the imaging volume.

Differing degrees of image quality within a single X-ray image can be desirable as a physician may wish to view a small region of interest (ROI), such as a heart during a cardiac procedure, with very high-quality images, e.g. good contrast-to-noise, while generally monitoring the surrounding area. Since prolonged X-ray exposure can have adverse health effects, it can be beneficial to use a lower amount of X-ray flux to image areas outside of the ROI. Source-to-detector distance, source size, detector size, or other parameters of imaging geometry may be configured to create a central region, e.g. region imaged by both source-detector pairs, that is the size of a probable region of interest for a given application or range of applications. Alternatively, a system may be designed such that the region receiving flux from both X-ray sources is large enough to encompass the full width of a human body. In this embodiment, a patient may be positioned such that an entire plane or planes of interest can be imaged with high contrast-to-noise and low out-of-plane blurring.

Fields of view of embodiments of the present invention may be circular, square, polygonal, rectangular, trapezoidal, triangular, or any other shape, e.g. as determined by source and detector geometry. A field of view may have a maximum diameter or width of 5 to 10 cm, 10 to 15 cm, 15 to 20 cm, 20 to 25 cm, 25 to 30 cm, 30 to 35 cm, 35 to 40 cm, 40 to 45 cm, or 45 to 50 cm, inclusive, or any integer or non-integer number of centimeters within these enumerated values. For example, a field of view may have a diameter of 30, 31, 32, 33, 34, 35, 36, 37, 38, 39, or 40 cm, inclusive, or any non-integer between these enumerated values. For some applications, a field of view may have a diameter or width of less than 5 cm or greater than 40 cm.

For example, one embodiment of the present invention comprises two tomosynthetic source-detector pairs each having an individual field of view with a diameter of approximately 20 cm and a total field of view when positioned at a minimum possible angle of approximately 35 cm. Source faces in this embodiment may be circular and may have a diameter of 10". Detector faces may be rectangular and may be 10 cm by 5 cm.

Since each multi-focal spot source in embodiments of the present invention may have an amount of non-emissive, e.g. dead, space along the edges of its face due to source housing, connections to the target material, or other support structures, a gap in emissive locations may exist between the two source faces when positioned in the configuration of FIG. 6. This gap may affect the size or shape of the imaging volume or maximum field of view. Depending on the positioning of a patient relative to the source for a give application, the effect on the imaging volume may or may not be detrimental.

Figure 7:
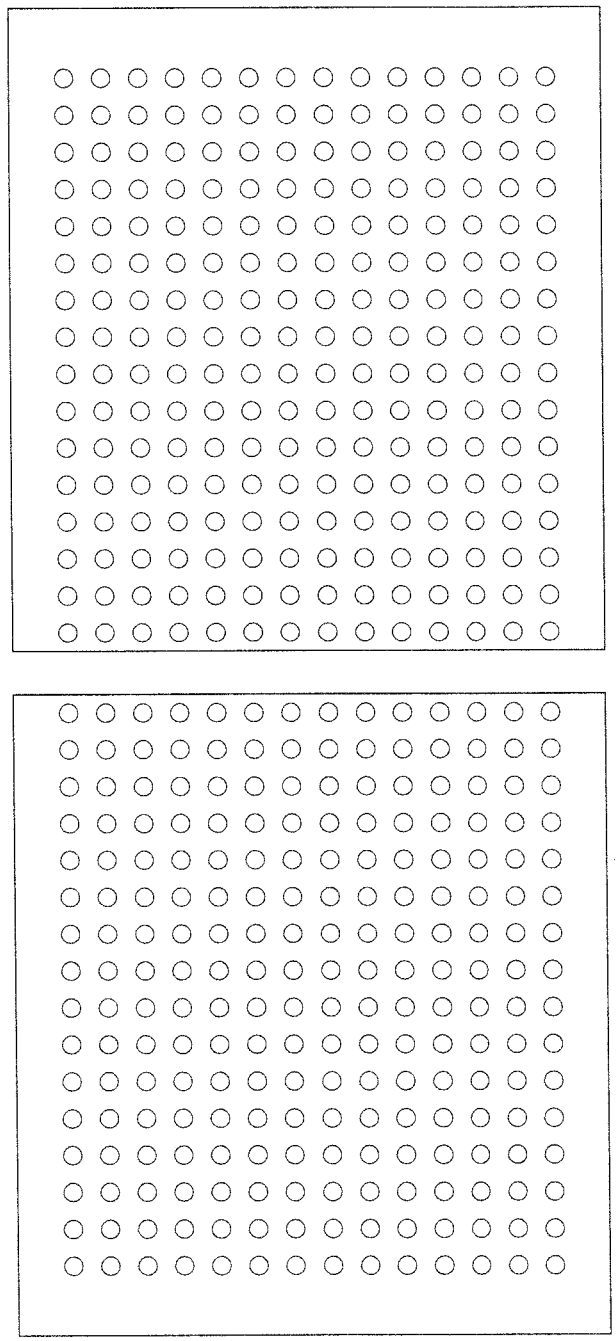
FIG. 7 is a diagram illustrating two sources configured to minimize the non-emissive surface existing between their adjacent edges in one embodiment of the present invention.

FIG. 7 is a diagram illustrating two multi-focal spot sources of one embodiment of the present invention configured to minimize the distance from emissive locations on one source to those on the other when the sources are positioned adjacently, e.g. with a minimum angle between source-detector pairs. The focal spot pattern across the faces of two sources in this embodiment may resemble the pattern of focal spots on a single, large-area multi-focal spot when they are placed in contact adjacently. For example, two scanning-beam sources may be fabricated with emissive target screens extending very close to edges of the source faces, reducing dead area along edges at which two source faces meet. Other types of source pairs may be configured to minimize a gap in the emissive surface, including a pair of nanotube arrays or any other pair of sources with little to no dead space along two adjacent edges. In these embodiments, a gap may be 2 cm, 3 cm, 4 cm, 5 cm, 6 cm, 7 cm, 8 cm, 9 cm, 10 cm, or a non-integer number of centimeters between these enumerated values. A gap may also be between 10 and 15 cm, 15 and 20 cm, 25 and 30 cm, 30 and 35 cm, 35 and 40 cm, 40 and 45 cm, or 45 and 50 cm, inclusive.

In one embodiment of the present invention, two scanning beam sources configured with minimal non-emissive area along adjacent edges and two photon-counting element-array detectors may be attached to two C-arms, e.g. such that each C-arm has a source on one end and a photon-counting detector on the opposing end. The two C-arms may be connected to one another by a joint aligned with an isocenter of the two source-detector pairs. Either the joint or another point on either C-arm may be connected to a support structure.

Figure 8:
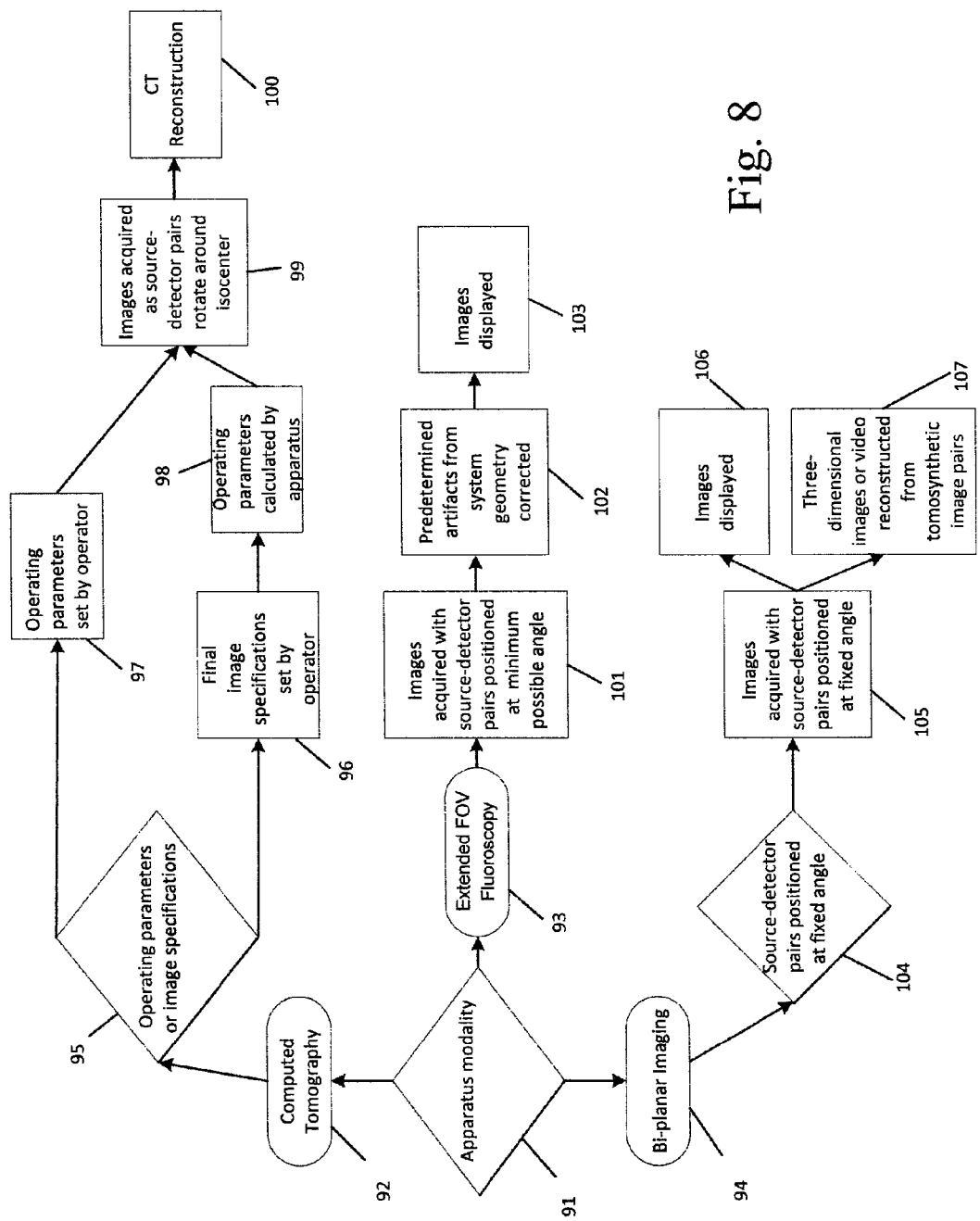
FIG. 8 is a diagram illustrating a relationship between three modalities of an apparatus in one embodiment of the present invention.

FIG. 8 is a diagram illustrating a relationship between aspects of three modalities of an embodiment of the present invention. In the embodiment of FIG. 8, an apparatus modality may be selected, as indicated by decision block 91. The modality may be for example a computed tomography modality 92, an extended-FOV fluoroscopy modality 93, or a bi-planar imaging modality 94. In one embodiment, in computed tomography modality 92 the apparatus may allow election in a decision block 95 to either set operating parameters, e.g. rotation speed, frame rate, etc. in option 97, or image specifications, e.g. final image resolution, in option 96. Operating parameters may be calculated in step 98 if a user selects option 96. Alternatively, a system may only provide option 96 or only provide option 97 under computed tomography modality 95. The system can implement the operating parameters from option 97 or step 98, acquiring images while rotating two or more source-detector pairs around an isocenter, as in step 99. Any type of CT reconstruction method can be utilized to generate a three-dimensional image in step 100.

For extended-FOV fluoroscopy modality 93 source-detector pairs of the system may be aligned at a near-zero minimum angle, e.g. with sources or detectors in contact adjacently. In step 101 a single set of image data may be acquired in this configuration or image data may be continuously acquired. If predetermined artifacts of system geometry are present in acquired images, they may be corrected in step 102 prior to displaying an image or video in step 103. Alternatively, a single source-detector pair may be utilized in extended-FOV fluoroscopy modality 93 if the field of view provided by the single source-detector pair is sufficient for a given application.

For bi-planar imaging modality 94 source-detector pairs may be positioned at any angle relative to one another in step 105. An image, images, or video can be displayed in step 106. If the apparatus comprises tomosynthetic source-detector pairs, then a three-dimensional image or video may also be reconstructed from two bi-planar data sets in step 107.

Other embodiments of the present invention utilize multiple modalities of an imaging system capable of at least three different imaging procedures in conjunction with one another, potentially to optimize the accuracy or registration of one or more of these modalities.

Registration may refer to the determination of a spatial relationship between multiple views, e.g. image data sets, of the same object or imaging volume, for example by selecting a reference data set and transforming coordinates of any other data sets into the coordinates of the reference data set. Accurate image registration can properly combine or overlay multiple data sets. Registration can be achieved by feature recognition, intensity mapping, or other methods relating data sets to the reference data set.

In one embodiment of the present invention, a three-dimensional image can be reconstructed from two bi-planar images acquired with multi-focal spot sources. In this embodiment, a CT data set can also be acquired with the same source-detector pairs used for bi-planar imaging. A lack of relative motion between the patient and imaging system can be achieved between the CT scan and bi-planar image acquisition. The CT data set can be used as a reference data set for registration of the two bi-planar images. A CT scan may also be utilized for registration of images acquired via other modalities of the imaging system, e.g. fluoroscopy, and with an imaging system comprising point sources rather than multi-focal spot sources.

In other embodiments of the present invention, imaging artifacts from insufficient data can be alleviated with a CT scan taken with little or no motion between the patient and imaging system during the transition from a CT to another imaging modality. Data from a preliminary or secondary CT scan can be used as a prior, e.g. a Bayesian prior, for reconstruction. Alternatively, another method of improving reconstructions with an additional data set may be used. In one such embodiment, two bi-planar tomosynthetic data sets can be reconstructed to form a three-dimensional image using MLEM, ML-TR, OSEM, ML-TR in an OSEM framework, or any other iterative or non-iterative reconstruction algorithm. The value of a given pixel or voxel from the preliminary CT dataset can be incorporated as a constraint, factor, or other term when determining probable pixel or voxel values via likelihood maximization or another method of the reconstruction algorithm.

Interventional procedures can often be planned based on an image or series from a preliminary CAT scan, which, for example, shows a tumor or other malignancy and surrounding internal features. This preliminary CAT scan may have been completed relatively long before, e.g. days, weeks, or months before, the interventional procedure. Internal features of a patient can change between the time at which the CAT scan completed and the time of the procedure, e.g. from weight loss or malignancy growth.

In one embodiment of the present invention, a CT modality of an imaging system comprising a set of source-detector pairs may be utilized directly before an interventional procedure. The interventional procedure may be guided by a fluoroscopy modality of the same imaging system. This embodiment allows a CT scan to be quickly completed before an interventional procedure without moving the patient or imaging system. A lack of relative motion between the patient and apparatus can result in this preliminary CT scan providing absolute locations or coordinates of internal features within the patient where they may be during the procedure.

In another embodiment of the present invention, an interventional procedure requiring some amount of three-dimensional information in a localized region, e.g. in the cardiac region for placement of an ablative device, can be completed using bi-planar imaging. A fast CT scan can be taken prior to bi-planar imaging, and the third-dimension coordinate of features seen in the two bi-planar two-dimensional images can be determined by comparison to the three-dimensional CT image or map.

Embodiments of the present invention may also be useful for verification or validation following an interventional procedure. For example, in one embodiment of the present invention, an interventional procedure may be completed under fluoroscopic guidance, e.g. with two source-detector pairs positioned at a minimum possible angle. A CT image may then be acquired by rotating the two source-detector pairs outward in opposite directions from the minimum angle configuration. If the three-dimensional image validates the success of the procedure, a physician may proceed to remove any implements within the patient and close incisions. If the three-dimensional image shows remaining malignancy or other issues, the source-detector pairs may be re-positioned for real-time image guidance and the procedure continued.

Figure 9:
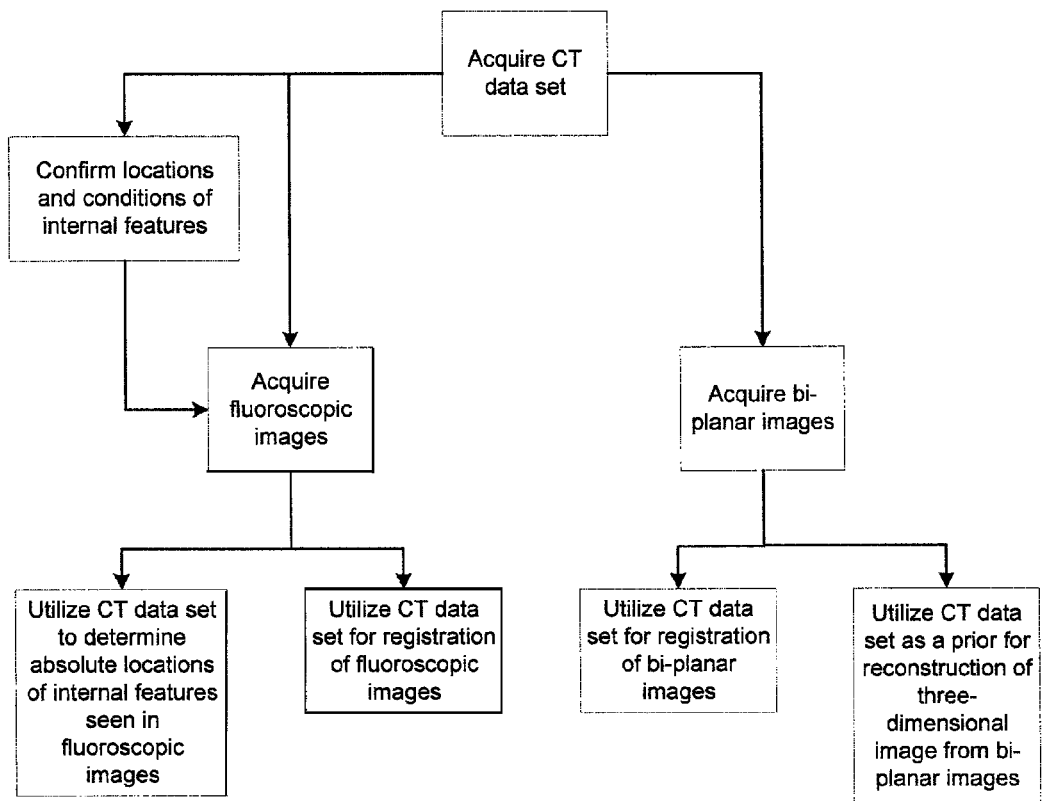
FIG. 9 is a flowchart illustrating a number of manners in which two or more modalities of an imaging apparatus may be utilized in conjunction with one another in an embodiment of the present invention.

FIG. 9 is a flowchart illustrating a number of manners in which modalities of an imaging apparatus may be utilized in a number of embodiments of the present invention. As previously described, two source-detector pairs can be utilized to acquire a CT data set. The same source-detector pairs can then be positioned for fluoroscopy, e.g. at a minimum possible angle, or bi-planar imaging. If fluoroscopy is being used as guidance for an interventional or surgical procedure, it may be valuable to determine or confirm the locations and conditions of internal features being targeted by the procedure. The CT data set may be utilized to determine absolute locations of internal features seen in fluoroscopic images, including third-dimension locations. It may also be used for registration of fluoroscopic images, e.g. to combine the views taken by two source-detector pairs in this embodiment. Similarly, a CT data set can be used for registration of bi-planar images or as a prior for reconstruction of a three-dimensional image, if the bi-planar images are tomosynthetic.

Embodiments of the present invention may utilize other combinations of the modalities of an apparatus comprising two source-detector pairs that can improve imaging speed, registration, or quality. Bi-planar imaging may be performed before or after extended-FOV fluoroscopy, extended-FOV fluoroscopy before or after CT, CT before or after bi-planar imaging, and so forth, where acquisition of each type of image by a single apparatus can allow for there to be little to no intermediate motion between a patient and the imaging.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A method of medical imaging comprising:
rotating a first X-ray source-detector pair through a first set of angles around an axis of rotation;
simultaneously rotating a second X-ray source-detector pair through a second set of angles around said axis of rotation, wherein said first set of angles and said second set of angles do not overlap;
acquiring image data from said first X-ray source-detector pair and said second X-ray source-detector pair during rotation; and
storing said image data to form a computed tomography dataset.

2. The method of claim 1 wherein said first set of angles and said second set of angles each comprise at least 90 degrees.

3. The method of claim 1 further comprising:
completing rotation of the first X-ray source-detector pair through the first set of angles and the second X-ray source-detector pair through the second set of angles in less than 3 seconds.

4. The method of claim 1 further comprising:
fixing positions of said first X-ray source-detector pair and said second X-ray source-detector pair at a predetermined angle of separation; and
acquiring images from said first X-ray source-detector pairs and said second X-ray source-detector pair while stationary.

5. The method of claim 4 further comprising:
utilizing said computed tomography dataset for registration of said images.

6. The method of claim 1 wherein source of said first X-ray source-detector pair is configured to emit radiation from a plurality of discrete locations on its face.

7. The method of claim 1 wherein source of said first X-ray source detector-pair is a point source.

8. A method of medical imaging comprising:
rotating two X-ray source-detector pairs around an imaging volume, wherein sources of said X-ray source-detector pairs are configured to emit radiation from pluralities of discrete locations on their faces;
acquiring a computed tomography dataset during rotation of said two X-ray source-detector pairs;
fixing said two X-ray source-detector pairs at a predetermined angle relative to one another;
acquiring image data from said two X-ray source-detector pairs while stationary at said predetermined angle relative to one another;
reconstructing a three-dimensional image from said image data; and
utilizing said computed tomography dataset as a prior for reconstruction of said three-dimensional image.

9. The method of claim 8 wherein said prior is a Bayesian prior.

10. The method of claim 8 wherein said predetermined angle is between 80 and 100 degrees, inclusive.

11. The method of claim 8 further comprising:
reconstructing said three-dimensional image using a maximum-likelihood expectation maximization in voxel space.

12. The method of claim 8 further comprising:
reconstructing said three-dimensional image using an ordered-subset expectation maximization framework.

13. The method of claim 8 further comprising:
reconstructing said three-dimensional image using a maximum likelihood algorithm for transmission tomography.

14. The method of claim 8 further comprising:
correcting artifacts in said three-dimensional image using said computed tomography dataset.

* * * * *